(12) United States Patent
Liang et al.

(10) Patent No.: US 11,090,633 B2
(45) Date of Patent: Aug. 17, 2021

(54) CATALYST COMPOSITION FOR THE OXIDATIVE COUPLING OF METHANE

(71) Applicant: SABIC Global Technologies B.V., Bergen op Zoom (NL)

(72) Inventors: Wugeng Liang, Sugar Land, TX (US); David West, Sugar Land, TX (US); Hector Perez, Sugar Land, TX (US); Sagar Sarsani, Sugar Land, TX (US); Luanyi Elizabeth Li, Sugar Land, TX (US); Pankaj Gautam, Sugar Land, TX (US)

(73) Assignee: SABIC GLOBAL TECHNOLOGIES B.V., Bergen op Zoom (NL)

( * ) Notice: Subject to any disclaimer, the term of this patent is extended or adjusted under 35 U.S.C. 154(b) by 73 days.

(21) Appl. No.: 16/743,714

(22) Filed: Jan. 15, 2020

(65) Prior Publication Data

US 2020/0230576 A1 Jul. 23, 2020

Related U.S. Application Data

(60) Provisional application No. 62/794,027, filed on Jan. 18, 2019.

(51) Int. Cl.
| | |
|---|---|
| *B01J 23/30* | (2006.01) |
| *C07C 11/04* | (2006.01) |
| *C07C 2/84* | (2006.01) |
| *B01J 23/10* | (2006.01) |
| *B01J 21/08* | (2006.01) |
| *B01J 37/04* | (2006.01) |

(52) U.S. Cl.
CPC .............. *B01J 23/30* (2013.01); *B01J 21/08* (2013.01); *B01J 23/10* (2013.01); *B01J 37/04* (2013.01); *C07C 2/84* (2013.01); *C07C 11/04* (2013.01); *C07C 2521/08* (2013.01); *C07C 2523/02* (2013.01); *C07C 2523/04* (2013.01); *C07C 2523/10* (2013.01); *C07C 2523/30* (2013.01)

(58) Field of Classification Search
CPC ... B01J 23/30; B01J 23/10; B01J 21/08; B01J 37/04; B01J 23/002; B01J 2523/00; B01J 35/0006; B01J 2523/24; B01J 2523/3706; B01J 2523/3775; B01J 2523/3787; B01J 2523/3725; C07C 11/04; C07C 2/84; C07C 2521/08; C07C 2523/02; C07C 2523/10; C07C 2523/04; C07C 2523/30; Y02P 20/52
See application file for complete search history.

(56) References Cited

U.S. PATENT DOCUMENTS 4,695,668 A * 9/1987 Velenyi ................ B01J 23/002
585/415

FOREIGN PATENT DOCUMENTS

| WO | WO 2014/143880 | 9/2014 |
| WO | WO 2015/168601 | 11/2015 |
| WO | WO 2016/044428 | 3/2016 |

OTHER PUBLICATIONS

"Oxidative coupling of methane in the presence of O2 and CO2 over selected catalysts based on silica-supported metals or sodium tungstate" *Czasopismo Techniczne—Politechnika Krakowska* 2009, 106(4), 37-42.
Arndt et al., "Mn—Na2WO4/SiO2 as catalyst for the oxidative coupling of methane. What is really known?" *Applied Catalysis A: General* 2012, vol. 425-426, 53-61.
Bi et al., "Ionic conductivity and catalytic performance of A2BO4/lanthanum oxide (La2O3) catalysts for oxidative coupling of methane" *Journal of Natural Gas Chemistry* 1993, 2(3), 203-211.
Fang et al., "Oxidative Coupling of Methane on W—Mn Catalyst" *Journal of Molecular Catalysis (China)* 1992, 6(6), 427-433 (English Abstract).
Fang et al., "W—Mn" *Journal of Molecular Catalysis (China)* 1992, 8(4), 255-262 (No Translation Provided).
Palermo et al., "Critical Influence of the Amorphous Silica-to-Cristobalite Phase Transition on the Performance of Mn/Na2WO4/SiO2 Catalysts for the Oxidative Coupling of Methane" *Journal of Catalysis* 1998, 177, 259-266.
Wu et al., "La-promoted Na2WO4/Mn/SiO2 catalysts for the oxidative conversion of methane simultaneously to ethylene and carbon monoxide" *Applied Catalysis A: General* 2007, 323, 126-134.
Yu et al., "Oxidative coupling of methane over Na2WO4/CeO2 and related catalysts" *Journal of Catalysis* 1995, 154(1), 163-73.
Zavyalova et al., "Statistical Analysis of Past Catalytic Data on Oxidative Methane Coupling for New Insights into the Composition of High-Performance Catalysts" *ChemCatChem* 2011, 3(12), 1935-1947.

* cited by examiner

*Primary Examiner* — Ali Z Fadhel
(74) *Attorney, Agent, or Firm* — Norton Rose Fulbright US LLP

(57) ABSTRACT

A catalyst composition, suitable for producing ethylene and other $C_{2+}$ hydrocarbons from methane. The composition includes a blended product of two distinct catalyst components, blended at such synergistic proportions, that results in a catalyst having high $C_{2+}$ hydrocarbon selectivity while maintaining an overall sufficient catalyst activity and low ethyne selectivity. Methods for preparing such a catalyst composition and a process for producing $C_{2+}$ hydrocarbons using such a catalyst composition are provided.

19 Claims, No Drawings

CATALYST COMPOSITION FOR THE OXIDATIVE COUPLING OF METHANE

CROSS REFERENCE TO RELATED APPLICATIONS

This application claims the benefit of priority of U.S. Provisional Patent Application No. 62/794,027 filed Jan. 18, 2019, which is hereby incorporated by reference in its entirety.

FIELD OF INVENTION

The invention relates to the field of catalyst compositions used for the oxidative coupling of methane (OCM).

BACKGROUND

Ethylene is one of the most important building blocks in the chemical industry and maximizing its production while maintaining desired operating profits through technology advancements is important for all ethylene producers. Keeping such objective in mind, catalyst development for the industrial production of ethylene and other $C_{2+}$ hydrocarbons from methane is an area of research, which has attracted a lot of attention from both industry and academia. Methane is a widely available feedstock having high calorific value, and if oxidatively coupled, in presence of certain methane coupling catalysts, commercially high value chemicals such as ethylene and other $C_{2+}$ hydrocarbons, can be produced sustainably at high production margins. However, one significant challenge plaguing technologies related to the oxidative coupling of methane, is the issue of ensuring high catalyst selectivity towards $C_{2+}$ hydrocarbons while maintaining sufficient catalyst activity. As may be appreciated by one skilled in the art, any attempts to increase catalyst selectivity typically comes at the cost of reduced the catalyst activity. High catalyst selectivity, ensures the production of commercially viable $C_{2+}$ hydrocarbon products while limiting the production of undesirable byproduct, thereby improving catalyst efficiency and process economics. On the other hand, low catalyst activity ordinarily associated with high catalyst selectivity, requires a large catalyst loading and reactor volume to effect the desired catalyst performance, resulting in higher capital investment. In addition, ethylene production through coupling reactions, inevitably leads to the formation of ethyne which is a severe poison for downstream polymerization processes. Separation processes, such as distillation, however does not reduce ethyne concentration to the necessary benign levels while extraction techniques using organic solvents are not economically viable to be applied in all production plants. Alternatively, the majority of ethyne removal is managed by selective hydrogenation, which adds to the operating and capital costs. Thus, there is a need to develop catalysts having excellent selectivity for $C_{2+}$ hydrocarbons other than ethyne, while retaining acceptable levels of catalyst activity.

Attempts to develop such catalyst systems have been discussed in various publications. One such catalyst system reported to have high stability and excellent selectivity for $C_{2+}$ hydrocarbons, is the catalyst system represented by the general formula $Mn-Na_2WO_4/SiO_2$. Arndt et.al in their publication (Applied Catalysis A: General, Volumes 425-426, 28 May 2012, Pages 53-61), provides a general review article for such catalyst systems when used in methane coupling reactions. However, as described in the publication, $Mn-Na_2WO_4/SiO_2$ catalyst systems are susceptible to deactivation under certain processing conditions, thereby posing additional plant operation challenges. Wu et.al in their publication (Applied Catalysis A: General, Volume 323, Pages 126-134) describes a lanthanum promoted catalyst having suitable $C_{2+}$ hydrocarbon selectivity. Other published literature such as the published patent WO2015101345A1 (Published: July 2015) or EP3194070A2 (Published: July 2017) describe the use of mixed metal oxides having a specific combination of rare earth metals, suitable for oxidative coupling of methane while retaining high temperature stability. Although, the results described in such publications are encouraging in terms of addressing some of the concerns pertaining to the catalyst performance, as may be appreciated by a person skilled in the art and by way of this disclosure, that such catalyst systems having rare earth metal oxides, can still be further improved upon in terms of their selectivity and activity performance.

Thus, from the foregoing reasons, there remains a need to develop a catalyst composition for the oxidative coupling of methane, having one or more benefits of having high $C_{2+}$ hydrocarbons selectivity, specifically ethylene, while maintaining low selectivity for ethyne while retaining sufficient catalyst activity for producing $C_{2+}$ hydrocarbon mixture products.

SUMMARY

The invention relates to a composition, comprising a blended product of: (i) a first catalyst component represented by a general formula (I): $(AE_aRE1_bRE2_cAT_dO_x)$ wherein, (a) 'AE' represents an alkaline earth metal; (b) 'RE1' represents a first rare earth element; (c) 'RE2' represents a second rare earth element; and (d) 'AT' represents a third rare earth element 'RE3' or a redox agent selected from antimony, tin, nickel, chromium, molybdenum, tungsten; wherein, 'a', 'b', 'c' and 'd' represents relative molar ratio; wherein 'a' is 1; 'b' ranges from 0.1 to about 10; 'c' ranges from about 0.01 to about 10; 'd' ranges from 0 to about 10; 'x' balances the oxidation state; wherein, the first rare earth element, the second rare earth element and the third rare earth element, are different; and (ii) a second catalyst component represented by a general formula (II): $((AM)_2WO_4)_e/SiO_2$, wherein, $(AM)_2WO_4$ represents an alkali metal tungstate, wherein, 'AM' represents an alkali metal, wherein, 'e' represents relative weight ratio and ranges from about 0.02 to about 0.8 and wherein, the composition has a catalyst activity for the reaction of oxygen and methane of at least 100 times greater than that of the catalyst activity of the second catalyst component.

In some embodiments of the invention, the alkaline earth metal is selected from the group consisting of magnesium, calcium, strontium, barium, and combinations thereof. In some embodiments, the relative molar ratio 'b' ranges from about 0.5 to about 8. In some embodiments of the invention, the alkali metal tungstate is selected from the group consisting of lithium tungstate, sodium tungstate, potassium tungstate, rubidium tungstate, caesium tungstate and combinations thereof. In some embodiments of the invention, the alkaline earth metal (AE) is selected from the group consisting of magnesium, calcium, strontium, barium, and combinations thereof. In some embodiments of the invention, the first rare earth element (RE1), the second rare earth element (RE2), and the third rare element (RE3) are each independently selected from the group consisting of lanthanum, scandium, cerium, praseodymium, neodymium, promethium, samarium, europium, gadolinium, yttrium, terbium, dysprosium, holmium, erbium, thulium, ytterbium, lutetium, and combinations thereof.

In some preferred embodiments of the invention, the first catalyst component is present in an amount ranging from about 5 wt. % to about 95 wt. % of the total weight of the composition. In some other preferred embodiments of the invention, the second catalyst component is present in an amount ranging from about 5 wt. % to about 95 wt. % of the total weight of the composition. In some embodiments of the invention, the composition comprising the blended product of the first catalyst component and the second catalyst component, has a 90% oxygen conversion temperature (T(90%)° C.) ranging from 0% to about 20%, greater than 90% oxygen conversion temperature (T(90%)° C.) of the first catalyst component. In some aspects of the invention, the composition achieves a methane conversion ranging from about 10% to about 50%, when the composition is used in a process for producing $C_{2+}$ hydrocarbons from methane and oxygen. In some aspects of the invention, the composition has an effective $C_{2+}$ hydrocarbon selectivity greater than 70% of product formed, when the composition is used in a process for producing $C_{2+}$ hydrocarbons from methane and oxygen. In some embodiments of the invention, the composition comprising the blended product of the first catalyst component and the second catalyst component has an effective $C_{2+}$ hydrocarbon selectivity ranging from about 1% to about 10%, greater than effective $C_{2+}$ hydrocarbon selectivity of the first catalyst component. In some embodiments of the invention, the composition comprising the blended product of the first catalyst component and the second catalyst component has a catalyst activity of at least four times that of a redox agent promoted second catalyst component. In some aspects of the invention, relate to a method for preparing the composition comprising the blended product of the first catalyst component and the second catalyst component comprising (a) blending the first catalyst component in an amount ranging from about 5 wt. % to about 95 wt. %, of the composition with the second catalyst component in an amount ranging from about 95 wt. % to about 5 wt. % of the composition, and (b) forming the composition. In some aspects of the invention, a composition comprising a $C_{2+}$ hydrocarbon mixture product is formed using the composition comprising the blended product of the first catalyst component and the second catalyst component. In some embodiments of the invention, the $C_{2+}$ hydrocarbon mixture product comprises ethylene, ethane, ethyne, propene, propane, $C_4$-$C_5$ hydrocarbons, carbon dioxide, carbon monoxide and combinations thereof. In some aspects of the invention, relate to a process for producing a $C_{2+}$ hydrocarbon mixture product comprising (a) introducing a feed mixture comprising methane and oxygen in a reactor containing the composition comprising the blended product of the first catalyst component and the second catalyst component, (b) subjecting the feed mixture to a methane coupling reaction under conditions suitable to produce the $C_{2+}$ hydrocarbon mixture product and (c) recovering the $C_{2+}$ hydrocarbon mixture product after removing unconverted methane and steam from the $C_{2+}$ hydrocarbon mixture product. In some embodiments of the invention, methane to oxygen ratio ranges from about 2:1 to about 15:1. In some embodiments of the invention, the $C_{2+}$ hydrocarbon mixture product is produced at a reactor temperature ranging from about 400° C. to about 900° C.

Some aspects of the invention, relate to a composition, comprising a blended product of: (i) a first catalyst component, represented by a general formula (I): $(AE_aRE1_bRE2_cAT_dO_x)$ wherein, (a) 'AE' represents an alkaline earth metal; (b) 'RE1' represents a first rare earth element; (c) 'RE2' represents a second rare earth element; and (d) 'AT' represents a third rare earth element 'RE3' or a redox agent selected from antimony, tin, nickel, chromium, molybdenum, tungsten; wherein, 'a', 'c' and 'd' represents relative molar ratio; wherein 'a' is 1; 'b' ranges from 0.45 to about 10; 'c' ranges from about 0.01 to about 10; 'd' ranges from 0 to about 10; 'x' balances the oxidation state; wherein, the first rare earth element, the second rare earth element and the third rare earth element, are different and the first rare earth element, the second rare earth element, and the third rare element are each independently selected from the group consisting of lanthanum, scandium, cerium, praseodymium, neodymium, promethium, samarium, europium, gadolinium, yttrium, terbium, dysprosium, holmium, erbium, thulium, ytterbium, lutetium, and combinations thereof; wherein, the first catalyst component is present in an amount ranging from about 5 wt. % to about 95 wt. % of the total weight of the composition; and (ii) a second catalyst component represented by a general formula (II): $((AM)_2WO_4)_e/SiO_2$ wherein, $(AM)_2WO_4$ represents an alkali metal tungstate, wherein, 'AM' represents an alkali metal and wherein, 'e' represents relative weight ratio and ranges from about 0.02 to about 0.8; and wherein, the second catalyst component has a catalyst activity for oxidative coupling of methane of less than 1% of catalyst activity for oxidative coupling of methane of the blended product of the first catalyst component and the second catalyst component; and wherein the second catalyst component is present in an amount ranging from about 5 wt. % to about 95 wt. % of the total weight of the composition; wherein, the composition has a 90% oxygen conversion temperature (T(90%)° C.) ranging from 0% to about 20% greater than 90% oxygen conversion temperature (T(90%)° C.) of the first catalyst component; and wherein, the composition has a catalyst activity for the reaction of oxygen and methane, of at least 100 times greater than that of the catalyst activity of the second catalyst component.

In the context of the present invention, at least twenty embodiments are now described. Embodiment 1 is a composition. The composition includes a blended product of: (i) a first catalyst component, represented by a general formula (I): $(AE_aRE1_bRE2_cAT_dO_x)$ wherein, (a) 'AE' represents an alkaline earth metal; (b) 'RE1' represents a first rare earth element; (c) 'RE2' represents a second rare earth element; and (d) 'AT' represents a third rare earth element 'RE3' or a redox agent selected from antimony, tin, nickel, chromium, molybdenum, tungsten; wherein, 'a', 'b', 'c' and 'd' represents relative molar ratio; wherein 'a' is 1; 'b' ranges from 0.1 to 10; 'c' ranges from about 0.01 to about 10; 'd' ranges from 0 to about 10; 'x' balances the oxidation state; wherein, the first rare earth element, the second rare earth element and the third rare earth element, are different; and (ii) a second catalyst component, represented by a general formula (II): $((AM)_2WO_4)_e/SiO_2$ wherein, $(AM)_2WO_4$ represents an alkali metal tungstate, wherein, 'AM' represents an alkali metal; wherein, 'e' represents relative weight ratio and ranges from about 0.02 to about 0.8; and wherein, the composition has a catalyst activity for the reaction of oxygen and methane of at least 100 times greater than that of the catalyst activity of the second catalyst component. Embodiment 2 is the composition of embodiment 1, wherein the relative molar ratio 'b' ranges from 0.5 to 8. Embodiment 3 is the composition of embodiment 1, wherein the alkali metal tungstate is selected from the group consisting of lithium tungstate, sodium tungstate, potassium tungstate, rubidium tungstate, caesium tungstate and combinations thereof. Embodiment 4 is the composition of embodiment 1, wherein the first catalyst component is present in an amount ranging from about 5 wt. % to about 95 wt. % of the total weight of the composition. Embodiment 5 is the composition of embodiment 1, wherein the second catalyst component is present in an amount ranging from about 5 wt. % to about 95 wt. % of the total weight of the composition. Embodiment 6 is the composition of embodiment 1, wherein the alkaline earth metal is selected from the group consisting of magnesium, calcium, strontium, barium, and combinations thereof. Embodiment 7 is the composition of embodiment 2, wherein the alkaline earth metal is selected from the group consisting of magnesium, calcium, strontium, barium, and combinations thereof. Embodiment 8 is the composition of embodiment 1, wherein the first rare earth element, the second rare earth element, and the third rare element are each independently selected from the group consisting of lanthanum, scandium, cerium, praseodymium, neodymium, promethium, samarium, europium, gadolinium, yttrium, terbium, dysprosium, holmium, erbium, thulium, ytterbium, lutetium, and combinations thereof. Embodiment 9 is the composition of embodiment 1, wherein the composition has a 90% oxygen conversion temperature (T(90%)° C.) ranging from 0% to about 20%, greater than 90% oxygen conversion temperature (T(90%)° C.) of the first catalyst component. Embodiment 10 is the composition of embodiment 1, wherein the composition achieves a methane conversion ranging from about 10% to about 50%, when the composition is used in a process for producing $C_{2+}$ hydrocarbons from methane and oxygen. Embodiment 11 is the composition of embodiment 1, wherein the composition has an effective $C_{2+}$ hydrocarbon selectivity greater than 70% of product formed, when the composition is used in a process for producing $C_{2+}$ hydrocarbons from methane and oxygen. Embodiment 12 is the composition of embodiment 11, wherein the composition has an effective $C_{2+}$ hydrocarbon selectivity ranging from about 1% to about 10%, greater than effective $C_{2+}$ hydrocarbon selectivity of the first catalyst component. Embodiment 13 is the composition of embodiment 11, wherein the composition has a catalyst activity of at least four times that of a redox agent promoted second catalyst component. Embodiment 14 is a method for preparing the composition of embodiment 1 including the steps of (a) blending the first catalyst component in an amount ranging from about 5 wt. % to about 95 wt. % of the composition with the second catalyst component in an amount ranging from about 95 wt. % to about 5 wt. % of the composition, and (b) forming the composition. Embodiment 15 is a composition containing a $C_{2+}$ hydrocarbon mixture product, wherein the composition is formed using the composition of embodiment 1. Embodiment 16 is the composition of embodiment 15, wherein the $C_{2+}$ hydrocarbon mixture product contains ethylene, ethane, ethyne, propene, propane, $C_4$-$C_5$ hydrocarbons, carbon dioxide, carbon monoxide and combinations thereof. Embodiment 17 is a process for producing a $C_{2+}$ hydrocarbon mixture product including the steps of (a) introducing a feed mixture containing methane and oxygen in a reactor containing the composition of embodiment 1; (b) subjecting the feed mixture to a methane coupling reaction under conditions suitable to produce the $C_{2+}$ hydrocarbon mixture product ; and (c) recovering the $C_{2+}$ hydrocarbon mixture product after removing unconverted methane and steam from the $C_{2+}$ hydrocarbon mixture product. Embodiment 18 is the process of embodiment 17, wherein methane to oxygen ratio ranges from about 2:1 to about 15:1. Embodiment 19 is the process of embodiment 17, wherein the $C_{2+}$ hydrocarbon mixture product is produced at a reactor temperature ranging from about 400° C. to about 900° C. Embodiment 20 is a composition that is a blended product of: (i) a first catalyst component represented by a general formula (I): $(AE_aRE1_bRE2_cAT_dO_x)$ wherein, (a) 'AE' represents an alkaline earth metal; (b) 'RE1' represents a first rare earth element; (c) 'RE2' represents a second rare earth element; and (d) 'AT' represents a third rare earth element 'RE3' or a redox agent selected from antimony, tin, nickel, chromium, molybdenum, tungsten; wherein, 'a', 'b', 'c' and 'd' represents relative molar ratio; wherein 'a' is 1; 'b' ranges from 0.45 to about 10; 'c' ranges from about 0.01 to about 10; 'd' ranges from 0 to about 10; 'x' balances the oxidation state; wherein, the first rare earth element, the second rare earth element and the third rare earth element, are different and the first rare earth element, the second rare earth element, and the third rare element are each independently selected from the group consisting of lanthanum, scandium, cerium, praseodymium, neodymium, promethium, samarium, europium, gadolinium, yttrium, terbium, dysprosium, holmium, erbium, thulium, ytterbium, lutetium, and combinations thereof; wherein, the first catalyst component is present in an amount ranging from about 5 wt. % to about 95 wt. % of the total weight of the composition; and (ii) a second catalyst component represented by a general formula (II): $((AM)_2WO_4)_e/SiO_2$ wherein, $(AM)_2WO_4$ represents an alkali metal tungstate; wherein 'AM' represents alkali metal and wherein, 'e' represents relative weight ratio and ranges from about 0.02 to about 0.8; and wherein, the second catalyst component has a catalyst activity for oxidative coupling of methane of less than 1% of catalyst activity for oxidative coupling of methane of the composition; and wherein the second catalyst component is present in an amount ranging from about 5 wt. % to about 95 wt. % of the total weight of the composition; wherein, the composition has a 90% oxygen conversion temperature (T(90%)° C.) ranging from 0% to about 20% greater than 90% oxygen conversion temperature (T(90%)° C.) of the first catalyst component; and wherein, the composition has a catalyst activity for the reaction of oxygen and methane of at least 100 times greater than that of the catalyst activity of the second catalyst component.

Other objects, features and advantages of the invention will become apparent from the following figures, detailed description, and examples. It should be understood, however, that the figures, detailed description, and examples, while indicating specific embodiments of the invention, are given by way of illustration only and are not meant to be limiting. Additionally, it is contemplated that changes and modifications within the spirit and scope of the invention will become apparent to those skilled in the art from this detailed description. In further embodiments, features from specific embodiments may be combined with features from other embodiments. For example, features from some specific embodiments may be combined with features from any of the other embodiments. In further embodiments, additional features may be added to the specific embodiments described herein.

DETAILED DESCRIPTION

The invention is based, in part, on the discovery that a composition containing a catalyst, can be used for the oxidative coupling of methane with one or more benefits of having high $C_{2+}$ hydrocarbons selectivity, specifically ethylene, while maintaining low selectivity for ethyne and retaining sufficient catalyst activity for producing $C_{2+}$ hydrocarbon mixture products. Advantageously, the composition is formulated by synergistically blending two catalyst components, so as to catalyze the coupling reaction between methane and oxygen and produce a unique composition of $C_{2+}$ hydrocarbon mixture product while minimizing unconverted methane in the product stream.

The following includes definitions of various terms and phrases used throughout this specification.

The terms "about" or "approximately" or "substantially" are defined as being close to as understood by one of ordinary skill in the art. In some non-limiting embodiments the terms are defined to be within 1%, preferably, within 0.1%, more preferably, within 0.01%, and most preferably, within 0.001%.

The terms "wt. %", "vol. %", or "mol. %" refers to a weight, volume, or molar percentage of a component, respectively, based on the total weight, the total volume, or the total moles of material that includes the component. In a non-limiting example, 10 moles of a particular component present in a 100 moles of a material is 10 mol. % of component.

The use of the words "a" or "an" when used in conjunction with the term "comprising," "including," "containing," or "having" in the claims or the specification may mean "one," but it is also consistent with the meaning of "one or more," "at least one," and "one or more than one."

The words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The method of the invention can "comprise," "consist essentially of," or "consist of" particular ingredients, components, compositions, etc., disclosed throughout the specification.

Any numerical range used through this disclosure shall include all values and ranges there between unless specified otherwise. For example, a boiling point range of 50° C. to 100° C. includes all temperatures and ranges between 50° C. and 100° C. including the temperature of 50° C. and 100° C.

The term "overall $C_{2+}$ hydrocarbon" or "$C_{2+}$ hydrocarbon mixture product " as used in this disclosure means the hydrocarbon products produced using the inventive catalyst composition and having at least two carbon atoms and includes ethylene, ethane, ethyne, propene, propane, and $C_4$-$C_5$ hydrocarbons. The term "effective $C_{2+}$ hydrocarbon" as used in this disclosure means $C_{2+}$ hydrocarbon excluding ethyne and represents the portion of $C_{2+}$ hydrocarbon mixture product which is commercially useful for producing high value chemicals and/or materials, and indicates the selectivity of the catalyst composition towards such useful hydrocarbon products.

The term oxidative coupling of methane or "OCM" as referred or used through this disclosure means the oxidative coupling of methane or the reaction of methane and oxygen, for the production of $C_{2+}$ hydrocarbons from methane.

The term "catalyst activity"" as used throughout this disclosure means catalyst activity for the reaction of methane with oxygen whether or not it is expressly stated as such, unless expressly stated otherwise. The catalyst activity is proportional to the oxygen conversion at a specific temperature for example, at a temperature ranging from 650° C. to 700° C. and can be determined using a gas chromatograph and calculated using the equation: $k = -\text{Ln}(1-XO_2/100)$, (Eqn I), where $XO_2$ is the oxygen conversion rate. For the purposes of this invention, oxygen conversion can be measured by comparing the oxygen concentration at the outlet and inlet of an oxidative coupling of methane reactor, such reactor being a 2.3 mm ID quartz tube reactor having a feed mixture flow rate adjusted from about 40 sccm and a catalyst loading of 20 mg. A parameter which serves as a convenient proxy for catalyst activity is the temperature at which 90% of the oxygen conversion takes place, herein represented as (T(90%)° C.). In this way, lower values of (T(90%)° C.) indicate higher catalyst activity than do higher values of (T(90%)° C.). Alternatively, the catalyst activity of a catalyst component or a catalyst composition once measured, may be expressed relative to the catalyst activity of another catalyst component.

The term "redox agent" as used herein means substances or elements capable of undergoing or promoting or supporting both oxidation or reducing reactions. The term "negligible" as used in context of the catalyst activity of the second catalyst component means that the second catalyst component is inherently substantially inert towards the reaction of methane and oxygen and has a catalyst activity that is less than 1% of catalyst activity of the blended product of the first catalyst component and the second catalyst component. Alternatively, the term "negligible" as used in the context of the catalyst activity of the second catalyst component means that the blended product of the first catalyst component and the second catalyst component has a catalyst activity of at least 100 times greater than that of the catalyst activity of the second catalyst component.

The term "selectivity" to a desired product or products refers to how much desired product was formed divided by the total products formed, both desired and undesired. For purposes of the disclosure herein, the selectivity to a desired product is a % selectivity based on moles converted into the desired product. Further, for purposes of the disclosure herein, a $C_x$ selectivity (e.g., $C_2$ selectivity, $C_{2+}$ selectivity, etc.) can be calculated by dividing a number of moles of carbon (C) from $CH_4$ that were converted into the desired product (e.g., $C_{C2H4}$, $C_{C2H6}$, etc.) by the total number of moles of C from $CH_4$ that were converted (e.g., $C_{C2H4}$, $C_{C2H6}$, $C_{C2H2}$, $C_{C3H6}$, $C_{C3H8}$, $C_{C4S}$, $C_{CO2}$, $C_{CO}$, etc.). $C_{C2H4}$=number of moles of C from $CH_4$ that were converted into $C_2H_4$; $C_{C2H6}$=number of moles of C from $CH_4$ that were converted into $C_2H_6$; $C_{C2H2}$=number of moles of C from $CH_4$ that were converted into $C_2H_2$; $C_{C3H6}$=number of moles of C from $CH_4$ that were converted into $C_3H_6$; $C_{C3H8}$=number of moles of C from $CH_4$ that were converted into $C_3H_8$; $C_{C4S}$=number of moles of C from $CH_4$ that were converted into $C_4$ hydrocarbons ($C_{4S}$); $C_{CO2}$=number of moles of C from $CH_4$ that were converted into $CO_2$; $C_{CO}$=number of moles of C from $CH_4$ that were converted into CO; etc. A $C_{2+}$ hydrocarbon selectivity (e.g., selectivity to $C_{2+}$ hydrocarbons) refers to how much $C_2H_4$, $C_3H_6$, $C_2H_2$, $C_2H_6$, $C_3H_8$, $C_{5S}$ and $C_{4S}$ were formed divided by the total products formed, including $C_2H_4$, $C_3H_6$, $C_2H_2$, $C_2H_6$, $C_3H_8$, $C_{4S}$, $C_{5S}$, $CO_2$ and CO. As may be appreciated by a person ordinary skilled in the art and by way of this disclosure, for a catalyst component having negligible catalyst activity the selectivity will also be negligible.

The invention provides for a composition, containing a catalyst, comprising a blended product of: (a) a first catalyst component comprising an alkaline earth metal and at least two rare earth elements, and (b) a second catalyst component comprising an alkali metal tungstate compound supported on silica. Particularly, the rare earth elements of the first catalyst component, are present at such relative molar ratios, that when the first catalyst component is blended with the second catalyst component at specific proportions, the resultant composition can be used as a catalyst for the oxidative coupling of methane and produce $C_{2+}$ hydrocarbon mixture products with high selectivity while retaining sufficient catalyst activity.

In aspects of the invention, the first catalyst component is represented by a general formula (I): $(AE_aRE1_bRE2_cAT_dO_x)$ wherein, (a) 'AE' represents an alkaline earth metal; (b) 'RE1' represents a first rare earth element; (c) 'RE2' represents a second rare earth element; and (d) 'AT' represents a third rare earth element 'RE3' or a redox agent; wherein, 'a', 'b', 'c' and 'd' represents relative molar ratio; wherein 'a' is 1; 'b' ranges from 0.1 to about 10, alternatively from 0.5 to 8, alternatively from 0.9 to 2; 'c' ranges from about 0.01 to about 10, alternatively from about 0.07 to about 1, alternatively from about 0.07 to about 0.8; 'd' ranges from 0 to about 10, alternatively from about 0.1 to about 5; 'x' balances the oxidation state; wherein, the first rare earth (RE1) element, the second rare earth element (RE2) and the third rare earth element (RE3), are different. The term "different" as used herein means that each of the rare earth elements are different chemical elements. In some embodiments of the invention, 'AT' is a third rare element. In some other embodiments, 'AT' is a redox agent selected from antimony, tin, nickel, chromium, molybdenum, tungsten. In some embodiments of the invention, the alkaline earth metal (AE) is selected from the group consisting of magnesium, calcium, strontium, barium, and combinations thereof. In some preferred embodiments of the invention, the alkaline earth metal (AE) is strontium. In some embodiments of the invention, the first rare earth element (RE1), the second rare earth element (RE2), and the third rare element (RE3) are each independently selected from the group consisting of lanthanum, scandium, cerium, praseodymium, neodymium, promethium, samarium, europium, gadolinium, yttrium, terbium, dysprosium, holmium, erbium, thulium, ytterbium, lutetium, and combinations thereof. In some preferred embodiments, the first rare earth element is lanthanum and is present at relative molar ratio 'b' of 0.5 or 1.8. In some embodiments of the invention, the first catalyst component is present in an amount ranging from about 5 wt. % to about 95 wt. %, alternatively from about 10 wt. % to about 80 wt. %, alternatively from about 20 wt. % to about 60 wt. %, of the total weight of the composition. Without wishing to be limited by any particular theory, the incorporation of stable rare earth metal oxides imparts catalytic stability to the composition and mitigates risks of catalyst deactivation during the oxidative coupling reaction.

In some aspects of the invention, the second catalyst component is represented by a general formula (II): $((AM)_2WO_4)_e/SiO_2$, wherein, $(AM)_2WO_4$ represents an alkali metal tungstate; wherein, 'AM' represents alkali metal and wherein, 'e' represents relative weight ratio and ranges from about 0.02 to about 0.8, or alternatively from about 0.08 to about 0.5, or alternatively from about 0.1 to about 0.4, wherein, the composition having the blended product of the first catalyst activity and the second catalyst activity, has a catalyst activity for the reaction of oxygen and methane of at least 100 times, alternatively at 105 times, or alternatively at least 120 times greater, than that of the catalyst activity of the second catalyst component. In some aspects of the invention, the composition having the blended product of the first catalyst activity and the second catalyst component has a catalyst activity of about 105 times to about 150 times, alternatively 110 times to about 130 times, greater than that of the catalyst activity of the second catalyst component. In other words, the second catalyst component has a catalyst activity for the reaction of methane and oxygen of not greater than 1% of catalyst activity of the blended product of the first catalyst component and the second catalyst component. The second catalyst component has negligible catalyst activity towards oxidative coupling of methane reaction and contributes 1% or less to the catalyst activity of the inventive compositions contemplated under this invention. Alternatively, the second catalyst component has a catalyst activity with the 'k' value, obtained for the second catalyst component using Eqn I, of not greater than 1% of the 'k' value obtained for the blended product of the first catalyst component and the second catalyst component. For the purposes of comparing the catalyst activity of the blended product of the first catalyst component and the second catalyst component with that of the second catalyst component, the catalyst activity of the second catalyst component is given a base value, for example 1, and the catalyst activity of the blended product of the first catalyst component and the second catalyst component is compared with that base value.

The inventors surprisingly found as evidenced by way of Example 6, that even when the second catalyst component is free of metal promoters such as manganese or antimony, the catalyst performance in terms of selectivity and activity for the inventive catalyst compositions, are improved over catalyst systems which have metal promoted alkali metal tungstate. In some embodiments of the invention, the alkali metal tungstate is present in an amount ranging from about 15 wt. % to about 95 wt. %, alternatively from about 20 wt. % to about 60 wt. %, alternatively from about 25 wt. % to about 50 wt. %, of the total weight of the second catalyst component. In some embodiments of the invention, the alkali metal tungstate is selected from the group consisting of lithium tungstate, sodium tungstate, potassium tungstate, rubidium tungstate, caesium tungstate and combinations thereof. In some preferred embodiments, the alkali metal tungstate used is sodium tungstate. Without wishing to be bound by any specific theory, it is understood that silica $(SiO_2)$ functions as a catalyst support and may undergo phase transition to form a more inert crystalline alpha-cristobalite structure, which regulates the stability and selectivity of the second catalyst component during the course of the catalysis. In some embodiments of the invention, the second catalyst component is present in an amount ranging from about 5 wt. % to about 95 wt. %, alternatively from about 20 wt. % to about 90 wt. %, alternatively from about 40 wt. % to about 80 wt. %, of the total weight of the composition.

In some aspects of the invention, the invention provides to a method for preparing the composition comprising the blended product of the first catalyst component and the second catalyst component, comprising (a) blending the first catalyst component in an amount ranging from about 5 wt. % to about 95 wt. %, alternatively from about 10 wt. % to about 80 wt. %, alternatively from about 20 wt. % to about 60 wt. %, of the composition with the second catalyst component in an amount ranging from about 95 wt. % to about 5 wt. %, alternatively from about 90 wt. % to about 20 wt. %, alternatively from about 80 wt. % to about 40 wt. %, of the composition, and (b) forming the composition. In some embodiments of the invention, the method further comprises grinding and press sizing of the composition. In some aspects of the invention, the method further comprises the step of forming the composition to special shape for loading into reactors.

In embodiments of the invention, the first catalyst component can be prepared by a method involving the step of forming an aqueous catalyst precursor solution containing a mixture of (i) a compound containing the alkaline earth metal (AE), (ii) a compound containing the first rare earth element (RE1) (iii) a compound containing the second rare earth metal (RE2) and optionally, (iv) a compound containing the third rare earth metal (RE3) or the redox agent. Subsequently, the aqueous catalyst precursor solution can be dried and thereafter calcined to obtain the first catalyst component. The drying step can be carried out at a temperature ranging from about 90° C. to about 150° C., alternatively at a temperature ranging from about 110° C. to about 140° C., alternatively at a temperature ranging from about 115° C. to about 130° C. The calcination step can be carried out at a temperature ranging from about 700° C. to about 950° C., alternatively from about 750° C. to about 900° C., for at least 5 hours. Non-limiting examples of compounds used as a precursor material for the catalyst preparation containing the alkaline earth metal (AE), first rare earth element (RE1), second rare earth element (RE2), third rare earth element (RE3), redox agent, are nitrates, carbonates, acetates, halides, oxides, hydroxides and any combinations thereof.

In embodiments of the invention, the second catalyst component can be prepared by a method using the incipient wetness method or impregnation method involving the use of silica gel. The method involves the step of forming an aqueous solution of the alkali metal tungstate compound followed by addition of the aqueous solution to a dry silica gel material and forming an impregnated silica based catalyst precursor material. The precursor material can subsequently be dried overnight and thereafter calcined for at least 5 hours to obtain the second catalyst component. The drying step can be carried out at a temperature ranging from about 90° C. to about 150° C., alternatively at a temperature ranging from about 110° C. to about 140° C., alternatively at a temperature ranging from about 115° C. to about 130° C. The calcination step can be carried out at a temperature ranging from about 700° C. to about 1,000° C., alternatively from about 750° C. to about 850° C.

In aspects of the invention, a composition comprising a $C_{2+}$ hydrocarbon mixture product is formed using the composition containing the blended product of the first catalyst component and the second catalyst component. In aspects of the invention, $C_{2-}$ hydrocarbon mixture product comprises ethylene, ethane, ethyne, propene, propane, $C_4$-$C_5$ hydrocarbons, carbon dioxide, carbon monoxide and combinations thereof. In aspects of the invention, a process for producing a $C_{2+}$ hydrocarbon mixture product, using the composition containing the blended product of the first catalyst component and the second catalyst component is provided. The process comprises (a) introducing a feed mixture comprising methane and oxygen in a reactor containing the composition comprising the blended product of the first catalyst component and the second catalyst component (b) subjecting the feed mixture to a methane coupling reaction under conditions suitable to produce the $C_{2+}$ hydrocarbon mixture product and (c) recovering the $C_{2+}$ hydrocarbon mixture product after removing unconverted methane and steam from the $C_{2+}$ hydrocarbon mixture product. In some aspects of the invention, unconverted methane, and steam is removed from the $C_{2+}$ hydrocarbon mixture product. In some embodiments of the invention, the removal of unconverted methane and steam from the $C_{2+}$ hydrocarbon mixture product is effected using a distillation column. In some embodiments of the invention, the distillation column is a cryogenic distillation column. In some embodiments of the invention, the feed mixture comprising methane and oxygen may be preheated to a temperature ranging from about 400° C. to about 550° C., alternatively from about 450° C. to about 500° C., prior to introducing the feed mixture in the reactor for methane coupling. The reactor can comprise an adiabatic reactor, an autothermal reactor, an isothermal reactor, a tubular reactor, a cooled tubular reactor, a continuous flow reactor, a fixed bed reactor, a fluidized bed reactor, a moving bed reactor, and the like, or combinations thereof. In one preferred aspect of the invention, a 2.3 mm ID quartz tube reactor is used for the purposes of reacting oxygen with methane under conditions sufficient to effect the oxidative coupling of methane. In some aspects of the invention, the reactor can comprise an adiabatic reactor. In some aspects of the invention, the $C_{2+}$ hydrocarbon mixture product is produced at a reactor temperature ranging from about 400° C. to about 900° C., alternatively from about 600° C. to about 850° C., alternatively from about 700° C. to about 810° C. In some aspects of the invention, the reactor can comprise a catalyst bed comprising the composition capable of catalyzing the oxidative coupling of methane. In some embodiments of the invention, the ratio of methane to oxygen ratio ranges from about 2:1 to about 15:1, alternatively from about 4:1 to about 10:1, alternatively from about 5:1 to about 8:1. Advantageously, the inventive catalyst composition of the present invention is capable of operating and retaining its activity even when subjected to high methane to oxygen ratio without deterioration of catalyst performance. In some embodiments of the invention, the pressure in the reactor is maintained at a pressure sufficient to effect oxidative coupling of methane. The pressure may be maintained at a range of about 14.7 psi (ambient atmospheric pressure) to about 500 psi, alternatively at a range of about 14.7 psi (ambient atmospheric pressure) to about 200 psi, alternatively at a range of about 14.7 psi (ambient atmospheric pressure) to about 150 psi. In some embodiments of the invention, the feed mixture is introduced into the reactor at a gas hourly space velocity (GHSV) ranging from about 500 $h^{-1}$ to about 1,000,000 $h^{-1}$, alternatively from about 1,000 $h^{-1}$ to about 300,000 $h^{-1}$, alternatively from about 5,000 $h^{-1}$ to about 100,000 $h^{-1}$, alternatively from about 10,000 $h^{-1}$ to about 80,000 $h^{-1}$, alternatively from about 20,000 $h^{-1}$ to about 50,000 $h^{-1}$.

In some aspects of the invention, a composition comprising a $C_{2+}$ hydrocarbon mixture product is formed using the composition containing the blended product of the first catalyst component and the second catalyst component. In some aspects of the invention, unconverted methane, and steam is removed from the $C_{2+}$ hydrocarbon mixture product prior to determining selectivity of carbon products. The composition comprising the $C_{2+}$ hydrocarbon mixture product has a unique blend of high ethylene content with low ethyne content. In some other aspects of the invention, the composition containing the blended product of the first catalyst component and the second catalyst component has an ethyne selectivity ranging from about greater than 0 to 2%, alternatively from 0.2% to 1.8%, alternatively from 0.5% to 1.2%, of product formed when the composition is used in a process that makes $C_{2+}$ hydrocarbon mixture product from methane. In some aspects of the invention, the composition exhibits a synergistic improvement of $C_{2+}$ hydrocarbon selectivity upon blending the first catalyst component and the second catalyst component. In some embodiments of the invention, the composition has an effective $C_{2+}$ hydrocarbon selectivity greater than 70% of product formed, when the composition is used in a process for producing $C_{2+}$ hydrocarbon from methane and oxygen. In some embodiments of the invention, the composition has an effective $C_{2+}$ hydrocarbon selectivity ranging from about 74.5% to about 90%, alternatively from about 78% to about 82%, of product formed, when the composition is used in a process for producing $C_{2+}$ hydrocarbon from methane and oxygen. In some embodiments of the invention, the composition comprising the blended product of the first catalyst component and the second catalyst component has an effective $C_{2+}$ hydrocarbon selectivity ranging from about 1% to about 10%, alternatively from about 2% to about 8%, alternatively from about 3% to about 4%, greater than effective $C_{2+}$ hydrocarbon selectivity of the first catalyst component. The synergistic effect of selectivity for the inventive composition is particularly evident as the second catalyst component has negligible catalyst activity in an oxidative coupling of methane process and can be further appreciated by a skilled person by way of Example 6 and 7 of this disclosure. The catalyst performance of the second catalyst component has also been discussed in publications such as (Palermo, et al., J. of Catal., Vol. 177, pp. 259-266 (1998).The improved effective $C_{2+}$ hydrocarbon selectivity of the inventive catalyst composition, is particularly suitable for producing industrially useful, non-ethyne $C_{2+}$ hydrocarbon products with high selectivity. The selectivity property exhibited by the inventive catalyst composition, results in lowering of the overall heat produced during the coupling reaction, improving catalyst performance and aiding in controlling reactor operations.

As may be appreciated by a person skilled in the art, for any catalyst having catalyst activity which is not negligible, the selectivity and activity properties of a catalyst are generally of opposing attributes. In some aspects of the invention, the inventors surprisingly found that the composition comprising the blended product of the first catalyst component and the second catalyst component is able to retain sufficient catalyst activity even with an increase in the selectivity property of the catalyst. One suitable metric to express catalyst activity once measured, is by reporting the temperature (T(90%)° C.) at which the 90% of the oxygen present in the feed is converted or has reacted with methane. The change in the value of (T(90%)° C.) is inversely proportional to the catalyst activity of the catalyst composition. An increase in the (T(90%)° C.) indicates reduced catalyst activity while lowering of (T(90%)° C.) is indicative of increased catalyst activity. As the overall oxidative coupling reaction is exothermic in nature, lower the temperature at which 90% oxygen conversion is achieved, the better is the catalyst activity. In other words, with an increase in catalyst selectivity, the temperature at which 90% oxygen conversion is going to be achieved is expected to increase substantially (lowering of catalyst activity). In some embodiments of the invention, the composition comprising the blended product of the first catalyst component and the second catalyst component, has a 90% oxygen conversion temperature (T(90%)° C.) ranging from 0% to about 20%, alternatively ranging from about 3% to about 15%, alternatively from about 5% to about 10%, greater than 90% oxygen conversion temperature (T(90%)° C.) of the first catalyst component. In some preferred embodiments of the invention, the composition comprising the blended product of the first catalyst component and the second catalyst component has 0% change in the (T(90%)° C.) when compared with the first catalyst component. In some aspects of the invention, the composition achieves a 90% oxygen conversion at a temperature ranging from about 600° C. to about 780° C., alternatively from about 620° C. to about 720° C., alternative from about 650° C. to about 700° C., when the composition is used in a process for producing $C_{2+}$ hydrocarbon from methane and oxygen. Although in some instance, there is an increase in the temperature for the 90% oxygen conversion T(90%)° C., the increase is within reasonable limits to allow for sufficient catalyst activity of the composition to form $C_{2+}$ hydrocarbon product with excellent methane conversion.

In some aspects of the invention, the composition has a catalyst activity of at least four times, alternatively at least ten times, alternatively at least thirty times, than that of a redox agent promoted/metal promoted second catalyst component. Although, with an increase in the catalyst activity, catalyst selectivity towards $C_{2+}$ hydrocarbon products was expected to reduce significantly. However, as will be appreciated by way of inventive example (Example 6) shown in this disclosure, catalyst selectivity decreased not more than 1.2% in some embodiments of the invention, while surprisingly the selectivity increased by about 1.5% in some other embodiments of the invention during the course of catalysis. Non-limiting example of redox agent/metal promoters include manganese, tungsten, bismuth, antimony, tin, cerium, praseodymium, vanadium, chromium, iron, cobalt and combinations thereof. The comparison of catalyst performance of the inventive catalyst compositions with that of the redox agent/metal promoted second catalyst component is particularly significant as some of the redox agent/metal promoted second catalyst component, have been reported in several publications as a promising catalyst system for oxidative coupling of methane. One such redox agent/metal promoted catalyst composition is a manganese promoted silica supported sodium tungstate composition of the general formula $Mn-Na_2WO_4/SiO_2$, which have been discussed in detail by Arndt et.al, in their publication. Further, the comparison with the redox agent/metal promoted second catalyst system, further evidences the synergistic effect of blending the first catalyst component with the second catalyst component as contemplated in the invention.

In some aspects of the invention, the composition comprising the blended product of the first catalyst component and the second catalyst component, achieves methane conversion ranging from about 10% to about 50%, alternatively from about 15% to about 40%, alternatively from about 20% to about 35%, when the composition is used in a process for producing $C_{2+}$ hydrocarbon from methane and oxygen. The high methane conversion results in lower amounts of unconverted methane in the product stream, and thus reducing the need for deploying additional capital intensive separation techniques for product gas purification.

Accordingly, the invention includes embodiments that include compositions containing catalyst compositions that exhibit one or more benefits of having improved $C_{2+}$ hydrocarbon selectivity, specifically ethylene and other use useful hydrocarbons, while maintaining low selectivity for ethyne and retaining sufficient catalyst activity for producing $C_{2+}$ hydrocarbon mixture products. Advantageously, the invention now enables artisans to formulate compositions in such a manner so as to catalyze the coupling reaction between methane and oxygen to produce a unique composition of $C_{2+}$ hydrocarbon mixture products having improved content of $C_{2+}$ hydrocarbon without compromising on the catalyst activity.

Specific examples demonstrating some of the embodiments of the invention are included below. The examples are for illustrative purposes only and are not intended to limit the invention. It should be understood that the embodiments and the aspects disclosed herein are not mutually exclusive and such aspects and embodiments can be combined in any way. Those of ordinary skill in the art will readily recognize parameters that can be changed or modified to yield essentially the same results.

EXAMPLES

Example 1

Catalyst Composition Having the Formula $(Sr_1La_{0.5}Er_{0.3}Yb_{0.1}O_x)_{0.59}$—$(Na_2WO_4/SiO_2)_{0.41}$ with First Catalyst Component Present in an Amount of 59 wt. % and the Second Catalyst Component Present in an Amount of 41 wt. %

Purpose: Example 1 demonstrates the preparation and use of a composition comprising a catalyst, having the formula $(Sr_1La_{0.5}Er_{0.3}Yb_{0.1}O_x)_{0.59}$—$(Na_2WO_4/SiO_2)_{0.41}$. The composition is used for the production of $C_{2+}$ hydrocarbon mixture product with increased selectivity towards $C_{2+}$ hydrocarbon mixture product while retaining identical catalyst activity determined by way of (T(90%)° C.) measurement.

Materials: The following materials are procured and used for the synthesis of the composition.

TABLE 1

First catalyst component (inventive catalyst $(Sr_1La_{0.5}Er_{0.3}Yb_{0.1}O_x)_{0.59}$—$(Na_2WO_4/SiO_2)_{0.41}$)

| First catalyst component: $AE_aRE1_bRE2_cRE3_dO_x$ | Element used | Relative molar ratio | Precursor Material | Supplier |
|---|---|---|---|---|
| AE | Strontium (Sr) | a = 1.0 | Strontium Nitrate: $Sr(NO_3)_2$ | Sigma-Aldrich |
| RE1 | Lanthanum (La) | b = 0.5 | Lanthanum Nitrate $La(NO_3)_3$ | Sigma-Aldrich |
| RE2 | Erbium (Er) | c = 0.3 | Erbium Nitrate: $Er(NO_3)_3$ | Sigma-Aldrich |
| RE3 | Ytterbium (Yb) | d = 0.1 | Ytterbium Nitrate $Yb(NO_3)_3$ | Sigma-Aldrich |

TABLE 2

Second catalyst component (inventive catalyst $(Sr_1La_{0.5}Er_{0.3}Yb_{0.1}O_x)_{0.59}$—$(Na_2WO_4/SiO_2)_{0.41}$)

| Second catalyst component: $((AM)_2WO_4/SiO_2)$ | Material used | Weight content (%) | Precursor Material | Supplier |
|---|---|---|---|---|
| Silica | Silica gel | — | (Davisil Grade 646) | Sigma-Aldrich |
| $(AM)_2WO_4$ | Sodium Tungstate $(Na_2WO_4)$ | 50.0 | $Na_2WO_4 \cdot 2H_2O$ | Sigma-Aldrich |

Method for preparing the composition containing the catalyst of Example 1: The composition was prepared by the method of (a) blending the first catalyst component in an amount ranging from about 5 wt. % to about 95 wt. % of the composition, with the second catalyst component in an amount ranging from about 95 wt. % to about 5 wt. % of the composition, and (b) forming the composition. The method further included the step of grinding and press sizing the composition. More specifically, the method included the step of blending 5.9 g of the first catalyst component $(Sr_1La_{0.5}Er_{0.3}Yb_{0.1}O_x)$ with 4.1 g of the second catalyst component $(Na_2WO_4/SiO_2)$ followed by grinding and press sizing the resulting blend. The individual catalyst components, the first catalyst component and the second catalyst component were prepared as given below:

Method for Preparing the first catalyst component $(Sr_1La_{0.5}Er_{0.3}Yb_{0.1}O_x)$ of Example 1 The follow steps were followed for the synthesis of the first catalyst component 8.47 g of $Sr(NO_3)_2$, 8.66 g of $La(NO_3)_3 \cdot 6H_2O$, 5.32 g of $Er(NO_3)_3 \cdot H_2O$ and 1.76 g of $Yb(NO_3)_3 \cdot 6H_2O$ were all mixed and dissolved 40 ml water. The resulting material was dried overnight at a temperature of 125° C. and then calcined at a temperature of 900° C. for 6 hours under airflow and the first catalyst component $Sr_1La_{0.5}Er_{0.3}Yb_{0.1}O_x$ was subsequently obtained.

Method for preparing the second catalyst component $(Na_2WO_4/SiO_2)$ of Example 1: Incipient wetness method is used for the second catalyst component. Silica gel (2.94 g Davisil Grade 646) with size 35/60 mesh, was used after drying overnight. $Na_2WO_4 \cdot 2H_2O$ (3.36 g) was dissolved in deionized water (6.0 ml) and the solution obtained was added drop wise onto dried silica gel material. The resulting material was dried overnight at a temperature of 125° C. and then calcined at a temperature of 800° C. for 6 hours under airflow and the second catalyst component $Na_2WO_4/SiO_2$ was obtained with the active component loadings shown in Table 2.

Process for producing $C_{2+}$ hydrocarbon mixture product using the composition of Example 1: The composition obtained from the practice of Example 1, was thereafter used for producing $C_{2+}$ hydrocarbon mixture product using the process comprising (a) introducing a feed mixture comprising methane and oxygen in a reactor containing the composition of Example 1; thereafter (b) subjecting the feed mixture to a methane coupling reaction under conditions suitable to produce a $C_{2+}$ hydrocarbon mixture product and subsequently, (c) recovering the $C_{2+}$ hydrocarbon mixture product after removing any unconverted methane and steam. More particularly, the composition containing the catalyst obtained from Example 1, was placed in a 2.3 mm ID quartz tube, and was contacted with a feed mixture containing methane and oxygen. The ratio of methane to oxygen was adjusted to a ratio of 7.4:1 and the feed mixture flow rate was adjusted from 40 sccm. The catalyst loading in the reactor was 20 mg. The reactors were operated under ambient pressure. Under different reactor temperatures, catalyst performance was obtained. Products obtained were analyzed using online Gas Chromatograph having a thermal conductivity detector (TCD) and a flame ionization detector (FID).

The operating parameters for producing the $C_{2+}$ hydrocarbon mixture product is as given below:

TABLE 3

Operating Parameter used for producing $C_{2+}$ hydrocarbon mixture product

| Starting reactor temperature for testing (° C.) | End reactor temperature for testing (° C.) | Pressure inside reactor (psi) | Gas Hourly Space Velocity (GHSV) ($hr^{-1}$) |
|---|---|---|---|
| 600° C. | 850° C. | Ambient pressure, (14.7) | 115,589 |

For the purpose of evaluating the composition comprising the catalyst of Example 1, the individual catalyst components were tested for their efficacy in producing the $C_{2+}$ hydrocarbon mixture product. The first catalyst component ($Sr_1La_{0.5}Er_{0.3}Yb_{0.1}O_x$) was subjected to the same reaction condition and process steps as that of the composition of Example 1 ($Sr_1La_{0.5}Er_{0.3}Yb_{0.1}O_x)_{0.59}$—($Na_2WO_4/SiO_2)_{0.41}$. For the second catalyst component, it is known have almost no activity for the OCM reaction (Palermo, et al., J. of Catal., Vol. 177, pp. 259-266 (1998)).

Results: The performances obtained using the composition containing catalyst of Example 1 ($Sr_1La_{0.5}Er_{0.3}Yb_{0.1}O_x)_{0.59}$—($Na_2WO_4/SiO_2)_{0.41}$ and that obtained from the use of the constituent first catalyst component ($Sr_1La_{0.5}Er_{0.3}Yb_{0.1}O_x$) and the second catalyst component ($Na_2WO_4/SiO_2$) are tabulated below. The catalyst activity for each of inventive composition, the first catalyst component and the second catalyst component were calculated using Eqn I,: $k=-Ln(1-XO_2/100)$, (Eqn I), where $XO_2$ is the oxygen conversion rate and reported relative to the catalyst activity of the second catalyst component. The (T(90%)° C.) was also calculated by noting the temperature at which 90% of the oxygen conversion was achieved.

TABLE 4

Catalyst selectivity/Activity

|  | Example 1 ($Sr_1La_{0.5}Er_{0.3}Yb_{0.1}O_x)_{0.59}$—($Na_2WO_4/SiO_2)_{0.41}$ | First Catalyst Component ($Sr_1La_{0.5}Er_{0.3}Yb_{0.1}O_x$) | Second Catalyst Component ($Na_2WO_4/SiO_2$) |
|---|---|---|---|
| Overall $C_{2+}$ hydrocarbon selectivity (%) | 78.2 | 77.1 | Negligible |
| Ethyne selectivity (%) | 0.1 | 0.1 | Negligible |
| Effective $C_{2+}$ hydrocarbon selectivity (%) | 78.1 | 77.0 | Negligible |
| Catalyst activity expressed using (T(90%)° C.) | 725 | 725 | Negligible |
| Methane conversion (%) | 20.2 | 19.7 | Negligible |
| Catalyst activity of inventive composition compared to the second catalyst component | >100 | >100 | 1 |

The results from Table 4 indicate that the inventive composition obtained from the practice of Example 1 shows increased selectivity towards $C_{2+}$ hydrocarbon without adversely affecting the catalyst activity as indicated by the value of T(90%)° C., which remains constant. The catalyst activity of the inventive composition is at least 100 times greater than the catalyst activity of the second catalyst component. In other words, the second catalyst component has a catalyst activity 1% or less than the catalyst activity of the inventive composition. The low catalyst activity of the second catalyst component is also reflected in the selectivity value of the second catalyst component, as second catalyst component has negligible contribution to the selectivity property of the composition. From Table 5, it may be concluded that in accordance with some embodiments of the invention, the inventive composition surprisingly demonstrated an improved catalyst selectivity particularly towards the effective $C_{2+}$ hydrocarbon mixture product, while retaining the desired catalyst activity. With the T(90%)° C. remaining constant, the inventive composition of Example 1 demonstrates previously unseen benefits of enhancing selectivity towards the effective $C_{2+}$ hydrocarbon with no measurable deterioration of catalyst activity. Thus, such inventive compositions are potentially beneficial for the oxidative coupling of methane at an industrial scale.

Another significant benefit from the invention, is the improved methane conversion effected by the inventive catalyst composition of Example 1. With the increase in $C_{2+}$ hydrocarbon selectivity, the selectivity to CO and $CO_2$ are reduced, resulting in more oxygen availability for converting methane to more useful $C_{2+}$ hydrocarbon mixture product. As shown in Table 4, the methane conversion is increased from 19.7 to 20.2, a 2.5% increase.

TABLE 5

Change in selectivity and catalyst activity

| | % change in Effective $C_{2+}$ hydrocarbon selectivity | % change in T(90%)° C. |
|---|---|---|
| Inventive composition Example 1 | 1.4% increase | 0% (No change in catalyst activity) |

Example 2

Catalyst Composition Having the Formula $(Sr_1La_{1.8}Nd_{0.7}Yb_{0.10}O_x)_{0.2}$—$(Na_2WO_4/SiO_2)_{0.8}$ with First Catalyst Component Present in an Amount of 20 wt. % and the Second Catalyst Component Present in an Amount of 80 wt. %

Purpose: Example 2 has a similar purpose as that of Example 1, and demonstrates the preparation and use of a composition comprising a catalyst having the formula $(Sr_1La_{1.8}Nd_{0.7}Yb_{0.1}O_x)_{0.2}$—$(Na_2WO_4/SiO_2)_{0.8}$.

Materials: The materials used were same as reported under Example 1 except that Neodymium (Nd) was used as the second rare earth element. Further, the relative molar ratio of Lanthanum used was higher than that used under Example 1.

Method for preparing the composition containing the catalyst of Example 2: The composition containing the blended product of the first catalyst component and the second catalyst component was prepared in the same manner as described under Example 1, involving the step of blending 2 g of the first catalyst component $(Sr_1La_{1.8}Nd_{0.7}Yb_{0.1}O_x)$ with 8 g of the second catalyst component $(Na_2WO_4/SiO_2)$ followed by grinding and press sizing the resulting blend. The first catalyst component and the second catalyst component were prepared as given below:

Method for preparing the first catalyst component $(Sr_1La_{1.8}Nd_{0.7}Yb_{0.1}O_x)$ of Example 2: The following steps were followed for the synthesis of the first catalyst component 8.47 g of $Sr(NO_3)_2$, 34.55 g of $La(NO_3)_3 \cdot 6H_2O$, 12.28 g of $Nd(NO_3)_3 \cdot 6H_2O$ and 1.8 g of $Yb(NO_3)_3 \cdot 5H_2O$ were mixed and dissolved 100 ml water. The resulting material was dried overnight at a temperature of 125° C. and then calcined at a temperature of 900° C. for 6 hours under airflow and the first catalyst component $Sr_1La_{1.8}Nd_{0.7}Yb_{0.1}O_x$ was obtained.

Method for preparing the second catalyst component $(Na_2WO_4/SiO_2)$ of Example 2: The second catalyst component of Example 2 was prepared in the same manner as described for the second catalyst component of Example 1.

Process for producing $C_{2+}$ hydrocarbon mixture product using the composition of Example 2: The composition obtained from the practice of Example 2 was used for producing $C_{2+}$ hydrocarbon mixture product using the process and conditions as described under Example 1. The operating parameters for producing the $C_{2+}$ hydrocarbon mixture product was same as that practiced under Example 1. As shown under Example 1, for the purpose of evaluating the composition comprising the catalyst of Example 2, the individual catalyst components were tested for their efficacy in producing the $C_{2+}$ hydrocarbon mixture product using the same procedure practiced for Example 1.

Results: The $C_{2+}$ hydrocarbon mixture product obtained using the composition containing catalyst of Example 2 $(Sr_1La_{1.8}Nd_{0.7}Yb_{0.1}O_x)_{0.2}$—$(Na_2WO_4/SiO_2)_{0.8}$ and that obtained from the use of the constituent first catalyst component $(Sr_1La_{1.8}Nd_{0.7}Yb_{0.1}O_x)$ and the constituent second catalyst component $(Na_2WO_4/SiO_2)$ was analyzed using online Gas Chromatograph having a thermal conductivity detector (TCD) and a flame ionization detector (FID). The results obtained are tabulated below. The catalyst activity for each of inventive composition, the first catalyst component and the second catalyst component were calculated using Eqn I,: $k=-Ln(1-XO_2/100)$, (Eqn I), where $XO_2$ is the oxygen conversion rate and reported relative to the catalyst activity of the second catalyst component. The (T(90%)° C.) was also calculated by noting the temperature at which 90% of the oxygen conversion was achieved.

TABLE 6

Catalyst selectivity/Activity

| | Example 2 $(Sr_1La_{1.8}Nd_{0.7}Yb_{0.1}O_x)_{0.2}$—$(Na_2WO_4/SiO_2)_{0.8}$ | First Catalyst Component $(Sr_1La_{1.8}Nd_{0.7}Yb_{0.1}O_x)$ | Second Catalyst Component $(Na_2WO_4/SiO_2)$ |
|---|---|---|---|
| Overall $C_{2+}$ hydrocarbon selectivity (%) | 78.8 | 77.6 | Negligible |
| Ethyne selectivity (%) | 0.0 | 0.0 | Negligible |
| Effective $C_{2+}$ hydrocarbon selectivity (%) | 78.8 | 77.6 | Negligible |
| Catalyst activity expressed using (T(90%)° C.) | 650 | 650 | Negligible |
| Catalyst activity of inventive composition compared to the second catalyst component | >100 | >100 | 1 |

The results from Table 6, indicate that the inventive composition obtained from the practice of Example 2 shows increased selectivity towards $C_{2+}$ hydrocarbons without adversely affecting the catalyst activity as indicated by the value of $T(90\%)°$ C., which remains constant. The catalyst activity of the inventive composition of Example 2 is at least 100 times greater than the catalyst activity of the second catalyst component. In other words, the second catalyst component has a catalyst activity 1% or less than the catalyst activity of the inventive composition. The low catalyst activity is also reflected in the selectivity value of the second catalyst component as second catalyst component has insignificant contribution to the selectivity property of the composition. With the $T(90\%)°$ C. remaining constant as summarized in Table 7, the inventive composition of Example 2 demonstrates previously unseen benefits of enhancing selectivity towards the effective $C_{2+}$ hydrocarbon with no deterioration of catalyst activity and thus potentially beneficial for the oxidative coupling of methane at an industrial scale.

TABLE 7

| Change in selectivity and activity rate | | |
| --- | --- | --- |
|  | % change in $C_{2+}$ hydrocarbon selectivity | % change in $T(90\%)°$ C. |
| Inventive composition Example 2 | ~1.5% increase | 0% (No change in catalyst activity) |

Example 3

Catalyst Composition Having the Formula $(Sr_1La_{1.8}Nd_{0.7}Yb_{0.1}O_x)_{0.1}$—$(Na_2WO_4/SiO_2)_{0.9}$ with First Catalyst Component Present in an Amount of 10 wt. % and the Second Catalyst Component Present in an Amount of 90 wt. %

Purpose: Example 3 demonstrates the preparation and use of a composition comprising a catalyst having the formula $(Sr_1La_{1.8}Nd_{0.7}Yb_{0.1}O_x)_{0.1}$—$(Na_2WO_4/SiO_2)_{0.9}$. The composition under Example 3 has similar constituents as that of the catalyst composition developed from the practice of Example 2, except that different proportions of the first catalyst component and the second catalyst component was used.

Materials: The materials used were same as that described under Example 2.

Method for preparing the composition containing the catalyst of Example 3: The process practiced was same as that described under Example 1 except that 1 g of the first catalyst component $(Sr_1La_{1.8}Nd_{0.7}Yb_{0.1}O_x)$ was blended with 9 g of the second catalyst component $(Na_2WO_4/SiO_2)$ to form the composition. The first catalyst component and the second catalyst component, were prepared using the same method as that described under Example 1.

Process for Producing $C_{2+}$ hydrocarbon mixture product using the composition of Example 3: The process practiced, including the operating parameters, was same as that described under Example 1. The operating parameters for producing the $C_{2+}$ hydrocarbon mixture product was same as that practiced under Example 1.

Results: The $C_{2+}$ hydrocarbon mixture product obtained by using the composition containing the catalyst of Example 3 $(Sr_1La_{1.8}Nd_{0.7}Yb_{0.1}O_x)_{0.1}$—$(Na_2WO_4/SiO_2)_{0.9}$ and that obtained from the use of the constituent first catalyst component $(Sr_1La_{1.8}Nd_{0.7}Yb_{0.1}O_x$ and the second catalyst component $(Na_2WO_4/SiO_2)$ were analyzed and the results obtained are tabulated below. The catalyst activity for each of inventive composition, the first catalyst component and the second catalyst component were calculated using Eqn I: $k=-Ln(1-XO_2/100)$, (Eqn I), where $XO_2$ is the oxygen conversion rate and reported relative to the catalyst activity of the second catalyst component. The $(T(90\%)°$ C.) was also calculated by noting the temperature at which 90% of the oxygen conversion was achieved.

TABLE 8

| | Catalyst selectivity/Catalyst activity | | |
| --- | --- | --- | --- |
| | Example 3 $(Sr_1La_{1.8}Nd_{0.7}Yb_{0.1}O_x)_{0.1}$—$(Na_2WO_4/SiO_2)_{0.9}$ | First Catalyst Component $(Sr_1La_{1.8}Nd_{0.7}Yb_{0.1}O_x)$ | Second Catalyst Component $(Na_2WO_4/SiO_2)$ |
| Overall $C_{2+}$ hydrocarbon selectivity (%) | 78.7 | 77.6 | Negligible |
| Ethyne selectivity (%) | 0.1 | 0.0 | Negligible |
| Effective $C_{2+}$ hydrocarbon selectivity (%) | 78.6 | 77.6 | Negligible |
| Catalyst activity expressed using $(T(90\%)°$ C.) | 725 | 650 | Negligible |
| Catalyst activity of inventive composition compared to the second catalyst component | >100 | >100 | 1 |

The results from Table 8 indicate that the inventive composition obtained from the practice of Example 3, shows increased selectivity towards $C_{2+}$ hydrocarbons compared to the constituent first catalyst component $(Sr_1La_{1.8}Nd_{0.7}Yb_{0.1}O_x)$ with a minor reduction in the catalyst activity indicated by way of an increase in the $T(90\%)°$ C. value. The reduction in the $T(90\%)°$ C. is found to be within an acceptable limit such that the catalyst performance is not adversely affected. The catalyst activity of the inventive composition of Example 3 is at least 100 times greater than the catalyst activity of the second catalyst component. In other words, the second catalyst component has a catalyst activity 1% or less than the catalyst activity of the inventive composition of Example 3. The low catalyst activity is also reflected in the selectivity value of the second catalyst component as second catalyst component has negligible contribution to the selectivity property of the composition.

TABLE 9

Change in selectivity and catalyst activity

|  | % change in Effective $C_{2+}$ hydrocarbon selectivity | % change in $T(90\%)°$ C. |
|---|---|---|
| Inventive composition Example 3 | ~1.3% increase | 11.5% increase | component $(Na_2WO_4/SiO_2)$ followed by grinding and press sizing the resulting blend. The individual catalyst components, the first catalyst component and the second catalyst component were prepared as given in Example 1.

Process for producing $C_{2+}$ hydrocarbon mixture product using the composition of Example 4: The composition obtained from the practice of Example 4 was used for producing $C_{2+}$ hydrocarbon mixture product using the process and the operating parameters as described under Example 1.

Results: The $C_{2+}$ hydrocarbon mixture product obtained by using the composition containing the catalyst of Example 4 $(Sr_1La_{0.4}Er_{0.4}Nd_{0.1}O_x)_{0.3}$—$(Na_2WO_4/SiO_2)_{0.7}$ and that obtained from the use of the constituent first catalyst component $(Sr_1La_{0.4}Er_{0.4}Nd_{0.1}O_x)$ and the second catalyst component $(Na_2WO_4/SiO_2)$, were analyzed using online Gas Chromatograph having a thermal conductivity detector (TCD) and a flame ionization detector (FID). The results obtained are tabulated below. The catalyst activity for each of inventive composition, the first catalyst component and the second catalyst component were calculated using Eqn I,: $k=-Ln(1-XO_2/100)$, (Eqn I), where $XO_2$ is the oxygen conversion rate and reported relative to the catalyst activity of the second catalyst component. The $(T(90\%)°$ C.) was also calculated by noting the temperature at which 90% of the oxygen conversion was achieved.

TABLE 10

Catalyst selectivity/Activity

|  | Example 4 $(Sr_1La_{0.4}Er_{0.4}Nd_{0.1}O_x)_{0.3}$—$(Na_2WO_4/SiO_2)_{0.7}$ | First Catalyst Component $(Sr_1La_{0.4}Er_{0.4}Nd_{0.1}O_x)$ | Second Catalyst Component $(Na_2WO_4/SiO_2)$ |
|---|---|---|---|
| Overall $C_{2+}$ hydrocarbon selectivity (%) | 78.5 | 77.1 | Negligible |
| Ethyne selectivity (%) | 0.0 | 0.1 | Negligible |
| Effective $C_{2+}$ hydrocarbon selectivity (%) | 78.5 | 77.0 | Negligible |
| Catalyst activity expressed using $(T(90\%)°$ C.) | 765 | 725 | Negligible |
| Catalyst activity of inventive composition compared to the second catalyst component | >100 | >100 | 1 |

Example 4

Catalyst Composition Having the Formula $(Sr_1La_{0.4}Er_{0.4}Nd_{0.1}O_x)_{0.3}$—$(Na_2WO_4/SiO_2)_{0.7}$ with First Catalyst Component Present in an Amount of 30 wt. % and the Second Catalyst Component Present in an Amount of 70 wt. %

Purpose: Example 4 demonstrates the preparation and use of a composition comprising a catalyst having the formula $(Sr_1La_{0.4}Er_{0.4}Nd_{0.1}O_x)_{0.3}$—$(Na_2WO_4/SiO_2)_{0.7}$.

Materials: The materials used were same as that described under Example 2.

Method for preparing the composition containing the catalyst of Example 4: The composition of Example 4, was prepared in the method similar to what was outlined under Example 1. Specifically, the method included the step of blending 3 g of the first catalyst component $(Sr_1La_{0.4}Er_{0.4}Nd_{0.1}O_x)$ with 7 g of the second catalyst The results from Table 10 indicate that the inventive composition obtained from the practice of Example 4, shows an increased selectivity of nearly 2% towards effective $C_{2+}$ hydrocarbon compared to the constituent first catalyst component $(Sr_1La_{0.4}Er_{0.4}Nd_{0.1}O_x)$ with a minor reduction in the catalyst activity indicated by way of an increase in the $T(90\%)°$ C. value (an increase of 5.5%). The catalyst activity of the inventive composition of Example 4 is at least 100 times greater than the catalyst activity of the second catalyst component. In other words, the second catalyst component has a catalyst activity 1% or less than the catalyst activity of the inventive composition of Example 4. The low catalyst activity is also reflected in the selectivity value of the second catalyst component as second catalyst component has negligible contribution to the selectivity property of the composition.

TABLE 11

Change in selectivity and activity rate

| | % change in Effective $C_{2+}$ hydrocarbon selectivity | % change in T(90%)° C. |
|---|---|---|
| Inventive composition Example 4 | ~2% increase | 5.5% increase |

Example 5

Catalyst Composition Having the Formula $(Sr_1La_{0.4}Er_{0.4}Nd_{0.1}O_x)_{0.25}$—$(Na_2WO_4/SiO_2)_{0.75}$ with First Catalyst Component Present in an Amount of 25 wt. % and the Second Catalyst Component Present in an Amount of 75 wt. %

Purpose: Example 5 demonstrates the preparation and use of a composition comprising a catalyst having the formula $(Sr_1La_{0.4}Er_{0.4}Nd_{0.1}O_x)_{0.25}$—$(Na_2WO_4/SiO_2)_{0.75}$. The constituents are same as that described in Example 4 except that the first catalyst component and the second catalyst components were blended at a different proportion.

Materials: The material used were same as that described under Example 4.

Method for preparing the composition containing the catalyst of Example 5: The composition of Example 5, was prepared in the method similar to what was outlined under Example 1. Specifically, the method included the step of blending 2.5 g of the first catalyst component $(Sr_1La_{0.4}Er_{0.4}Nd_{0.1}O_x)$ with 7.5 g of the second catalyst component $(Na_2WO_4/SiO_2)$ followed by grinding and press sizing the resulting blend. The individual catalyst components, the first catalyst component and the second catalyst component were prepared as provided under Example 1.

Process for producing $C_{2+}$ hydrocarbon mixture product using the composition of Example 5: The composition obtained from the practice of Example 5 was used for producing $C_{2+}$ hydrocarbon mixture product using the process and operating parameters as described under Example 1.

Results: The $C_{2+}$ hydrocarbon mixture product obtained by using the composition containing the catalyst of Example 5 $(Sr_1La_{0.4}Er_{0.4}Nd_{0.1}O_x)_{0.25}$—$(Na_2WO_4/SiO_2)_{0.75}$ and that obtained from the use of the constituent first catalyst component $(Sr_1La_{0.4}Er_{0.4}Nd_{0.1}O_x)$ and the constituent second catalyst component $(Na_2WO_4/SiO_2)$, were analyzed using online Gas Chromatograph having a thermal conductivity detector (TCD) and a flame ionization detector (FID). The results obtained are tabulated below. The catalyst activity for each of inventive composition, the first catalyst component and the second catalyst component were calculated using Eqn I: $k=-Ln(1-XO_2/100)$, (Eqn I), where $XO_2$ is the oxygen conversion rate and reported relative to the catalyst activity of the second catalyst component. The (T(90%)° C.) was also calculated by noting the temperature at which 90% of the oxygen conversion was achieved.

TABLE 12

Catalyst selectivity/Activity

| | Example 5 $(Sr_1La_{0.4}Er_{0.4}Nd_{0.1}O_x)_{0.25}$—$(Na_2WO_4/SiO_2)_{0.75}$ | First Catalyst Component $(Sr_1La_{0.4}Er_{0.4}Nd_{0.1}O_x)$ | Second Catalyst Component $(Na_2WO_4/SiO_2)$ |
|---|---|---|---|
| Overall $C_{2+}$ hydrocarbon selectivity (%) | 80.3 | 77.1 | Negligible |
| Ethyne selectivity (%) | 0.1 | 0.1 | Negligible |
| Effective $C_{2+}$ hydrocarbon selectivity (%) | 80.2 | 77.0 | Negligible |
| Catalyst activity expressed using (T(90%)° C.) | 800 | 725 | Negligible |
| Catalyst activity of inventive composition compared to the second catalyst component | >100 | >100 | 1 |

The results from Table 12, indicate that the inventive composition obtained from the practice of Example 5 shows an increased selectivity of nearly 4.2% towards effective $C_{2+}$ hydrocarbon, compared to the constituent first catalyst component $(Sr_1La_{0.4}Er_{0.4}Nd_{0.1}O_x)$ with a minor reduction in the catalyst activity indicated by way of an increase in the T(90%)° C. value (an increase of 10.3%). The reduction in catalyst activity was found to be within acceptable limits without adversely affecting catalyst performance. The catalyst activity of the inventive composition of Example 5 is at least 100 times greater than the catalyst activity of the second catalyst component. In other words, the second catalyst component has a catalyst activity 1% or less than the catalyst activity of the inventive composition of Example 5. The low catalyst activity is also reflected in the selectivity value of the second catalyst component as second catalyst component has negligible contribution to the selectivity property of the composition.

TABLE 13

Change in selectivity and activity rate

| | % change in $C_{2+}$ hydrocarbon selectivity | % change in T(90%)° C. |
|---|---|---|
| Inventive composition Example 5 | ~4.2% increase | 10.3% increase |

Example 6

Comparative

Catalyst Composition Having the Formula Sb—Mn—Na$_2$WO$_4$/SiO$_2$ Represents the Second Catalyst Component Having Antimony and Manganese Promoters Purpose: Example 6 is used as a comparative example to compare the catalyst performance of the second catalyst component promoted by Antimony and Manganese (Sb—Mn—Na$_2$WO$_4$/SiO$_2$), with that of the performance obtained by using the inventive compositions prepared by the practice of Example 1-5. The comparison with the catalyst Sb—Mn—Na$_2$WO$_4$/SiO$_2$, is particularly useful as the comparison of catalyst performance of a promoted second catalyst component, with the catalyst performance of the inventive compositions will be able to provide support any assertion of the synergistic effect of blending the first catalyst component and the second catalyst component as contemplated in the invention. Further, the comparison of the results obtained from the inventive compositions of Example 1-5 with that of Example 6 is particularly pertinent, as metal promoted alkali metal tungstate compounds have been researched extensively as a promising OCM catalyst composition.

Material: The material used was same as that of the second catalyst component used in Example 1, except that manganese and antimony were used as a promoter.

Method of preparing the manganese promoted second catalyst component: Incipient wetness method was used for preparing the second catalyst component. Accordingly, Mn(NO$_3$)$_2$.4H$_2$O (1.73 g) was dissolved in deionized water (18.5 ml) and then added dropwise onto a silica gel material (18.6 g Davisil Grade 646), and the resulting manganese impregnated silica material was subsequently dried overnight. Na$_2$WO$_4$.2H$_2$O (1.22 g) was dissolved in deionized water (18.5 ml) and the solution obtained was added onto the dried manganese impregnated silica material obtained from the above step. The resulting material was dried overnight at a temperature of 125° C. and subsequently calcined at a temperature of 800° C. for 6 hours under airflow to obtain the final product. Subsequently, 0.11 g of Sb$_2$O$_3$ (with particle size of 80-200 nm) was mixed with deionized water (6.0 mL) to form a slurry. The slurry was then added onto 3.3 g of calcined reference catalyst (Mn—Na$_2$WO$_4$/SiO$_2$ reference catalyst) prepared as described above. The resulting mixture was dried overnight at 125° C. Antimony and manganese promoted second catalyst component Sb—Mn—Na$_2$WO$_4$/SiO$_2$ was obtained with an antimony (Sb) content of 3.3%, manganese (Mn) content of 1.9 wt. % and sodium tungstate content of Na$_2$WO$_4$ of 5 wt. %.

Process for producing $C_{2+}$ hydrocarbon mixture product using the composition of Example 6: The composition obtained from the practice of Example 6 was used for producing $C_{2+}$ hydrocarbon mixture product using the process as described under Example 1. The operating parameters for producing $C_{2+}$ hydrocarbon mixture product was same as that described for Example 1, except that 100 mg catalyst is loaded in the reactor during the performance testing, due to its lower activity. Since larger amount of catalyst is used, the reactor tube used is 4 mm, to reduce the reactor pressure drop.

Result: The $C_{2+}$ hydrocarbon mixture product obtained by using the composition (Sb—Mn—Na$_2$WO$_4$/SiO$_2$) was analyzed using an online Gas Chromatograph, having a thermal conductivity detector (TCD) and a flame ionization detector (FID). The results obtained are compared with the catalyst activity and the $C_{2+}$ hydrocarbon selectivity obtained from the use of the inventive composition prepared under Example 1-5 and summarized below:

TABLE 14

Catalyst selectivity/Activity

| | Ex. 6 (comparative) | Ex. 1 (inventive) | Ex. 2 (inventive) | Ex. 3 (inventive) | Ex. 4 (inventive) | Ex. 5 (inventive) |
|---|---|---|---|---|---|---|
| Relative catalyst activity compared to catalyst activity of Ex. 6. | 1.0 | 65.5 | 103.5 | 20.5 | 11.9 | 9.6 |
| Effective $C_{2+}$ hydrocarbon selectivity (%) | 79.0 | 78.1 | 78.8 | 78.6 | 78.6 | 80.2 |

From Table 14, it is evident that the inventive catalyst compositions, demonstrate improved catalyst activity over that of the composition obtained from the practice of Example 6. Particularly, it is evident that the inventive compositions have a catalyst activity several times higher than that of the redox agent promoted second catalyst component prepared under Example 6. In other words, the inventive catalyst compositions have a catalyst activity nearly ten times of that of the composition obtained from Example 6. From the data it is further observed, that catalyst selectivity is not adversely affected even with such a significant increase in catalyst activity. In fact, contrary to expectation, for the inventive composition obtained from the practice of Example 6, improved catalyst performance in terms of $C_{2+}$ hydrocarbon selectivity and catalyst activity, is observed over that of the Antimony (Sb) and Manganese (Mn) promoted second catalyst component. The findings from the results of Example 6 are particularly significant as the inventive catalyst compositions from Example 1-5, demonstrate improved catalyst activity with comparable selectivity to that of metal promoted alkali metal tungstate catalysts.

Example 7

Comparative

Catalyst Composition Having the Formula (Sr$_1$La$_{0.5}$Er$_{0.3}$Yb$_{0.1}$O$_x$)$_{0.39}$-(Quartz chips)$_{0.61}$ with the First Catalyst Component Present in an Amount of 39 wt. % and Quartz Chips Present in an Amount of 61 wt. %

Purpose: Example 7 demonstrates the significance of the second catalyst component (AM)$_2$WO$_4$ in bring about synergistic effect in the inventive catalyst compositions even when the second catalyst component inherently negligible catalyst activity towards oxidative coupling of methane.

Materials: The material used is same as that described under Example 1, except that quartz chips were blended in the composition to simulate the effect of low catalyst activity of the second catalyst component.

Method for preparing the composition containing the catalyst of Example 8: The composition of Example 7, was prepared by blending 3.9 g of the first catalyst component of Example 1, with 6.1 g of quartz chips.

Process for producing $C_{2+}$ hydrocarbon mixture product using the composition of Example 7: The composition obtained from the practice of Example 7 was used for producing $C_{2+}$ hydrocarbon mixture product using the process as described under Example 1. The operating parameters used for producing $C_{2+}$ hydrocarbon mixture product was same as that described for Example 1.

Results: The $C_{2+}$ hydrocarbon mixture product obtained by using the composition containing the catalyst of Example 7 $((Sr_1La_{0.5}Er_{0.3}Yb_{0.1}O_x)_{0.39}$-(Quartz chips)$_{0.61})$ was compared with the results obtained from the practice of Example 1:

TABLE 15

Catalyst selectivity/Activity

| | Example 7 (comparative) | Example 1 (inventive) | First catalyst component of Example 1 |
|---|---|---|---|
| Effective $C_{2+}$ hydrocarbon selectivity (%) | 77.5 | 78.2 | 77.1 |
| Catalyst activity expressed using (T(90%)° C.) | 800 | 725 | 725 |

The results from Table 15 indicate that the inventive composition of Example 1, formed by blending the first catalyst composition with the second catalyst composition, demonstrates an improved $C_{2+}$ hydrocarbon selectivity over the first catalyst component, while retaining the desired level of catalyst activity. In contrast, the blending of quartz chips with the first catalyst component, shows a marginal increase in the $C_{2+}$ hydrocarbon selectivity with a sharp decline in the catalyst activity, indicated by way of increase in the T(90%)° C. value (increase of ~10%). The purpose of using the quartz chips is to simulate the contribution of the second catalyst component in terms of contributing to the catalyst performance, as quartz chips and the second catalyst component of the inventive compositions are inherently inert or have negligible catalyst activity towards methane oxygen reaction. It can be concluded that, although the second catalyst component by itself has negligible catalyst activity and its inherent activity can be compared with that of the quartz chips, for each inventive composition (Examples 1-5) the blending of the first catalyst component and the second catalyst component results in a blended product having a synergistic property of improved $C_{2+}$ hydrocarbon selectivity while retaining the desired catalyst activity or in some embodiments a decline in catalyst activity within reasonable limits.

Summary—From the example section and as summarized under Table 16, it is evident that the inventive catalyst compositions obtained from Example 1-5, demonstrate improved effective $C_{2+}$ hydrocarbon selectivity without any adverse impact in the catalyst activity. In particular, the inventive compositions obtained from the practice of Example 1 and Example 2, unexpectedly demonstrated that the inventive catalyst compositions are able to retain their catalyst activity even with an improved $C_{2+}$ hydrocarbon selectivity. With the T(90%)° C. remaining constant, the inventive compositions of Example 1 and 2, demonstrate previously unseen benefits of enhancing selectivity towards the effective $C_{2+}$ hydrocarbons with no measurable deterioration of catalyst activity, and such compositions are therefore potentially beneficial for the oxidative coupling of methane at an industrial scale. Results from Example 6, further provides evidence of the technical advancement of the invention, by demonstrating significant increase in the catalyst activity of the inventive catalyst compositions over a redox agent/metal promoted second catalyst component, thereby demonstrating the synergistic effect of blending the first catalyst component and the second catalyst component, as contemplated in the invention. It may be further concluded from Example 6, that the synergistic combination of the first catalyst component and the second catalyst component improves the catalyst performance of the inventive composition by the fact that the second catalyst has negligible catalyst activity towards oxidative coupling of methane reaction and contributes 1% or less than the overall catalyst activity of the inventive compositions. Further, results from Example 7, reinforces the conclusions drawn from Example 6, by successfully demonstrating the synergistic effect of incorporating the otherwise inert or second catalyst component with the first catalyst composition, to create the inventive composition of Example 1.

TABLE 16

Summary of Catalyst selectivity/Activity

| | % change in $C_{2+}$ hydrocarbon selectivity | % change in T(90%)° C. | Change in catalyst activity |
|---|---|---|---|
| Inventive composition Example 1 $(Sr_1La_{0.5}Er_{0.3}Yb_{0.1}O_x)_{0.59}$—$(Na_2WO_4/SiO_2)_{0.41}$ | 1.3% increase compared to First Catalyst component | 0% | Increase in selectivity with no change in catalyst activity |
| Inventive composition Example 2 $(Sr_1La_{1.8}Nd_{0.7}Yb_{0.1}O_x)_{0.2}$—$(Na_2WO_4/SiO_2)_{0.8}$ | ~1.5% increase compared to First Catalyst component | 0% | Increase in selectivity with no change in catalyst activity |
| Inventive composition Example 3 $(Sr_1La_{1.8}Nd_{0.7}Yb_{0.1}O_x)_{0.1}$—$(Na_2WO_4/SiO_2)_{0.9}$ | ~1.3% increase compared to First Catalyst component | 11.5% increase | Increase in selectivity with decline in catalyst activity |
| Inventive composition Example 4 $(Sr_1La_{0.4}Er_{0.1}Nd_{0.1}O_x)_{0.3}$—$(Na_2WO_4/SiO_2)_{0.7}$ | ~2% increase compared to First Catalyst component | 5.5% increase | Increase in selectivity with decline in catalyst activity |

TABLE 16-continued

Summary of Catalyst selectivity/Activity

| | % change in $C_{2+}$ hydrocarbon selectivity | % change in T(90%)° C. | Change in catalyst activity |
|---|---|---|---|
| Inventive composition Example 5 $(Sr_1La_{0.4}Er_{0.4}Nd_{0.1}O_x)_{0.25}$—$(Na_2WO_4/SiO_2)_{0.75}$ | ~4.2% increase compared to First Catalyst component | 10.3% increase | Increase in selectivity with decline in catalyst activity |
| Comparative Example 7 $(Sr_1La_{0.5}Er_{0.3}Yb_{0.1}O_x)_{0.39}$-(Quartz chips)$_{0.61}$ | ~0.7% decrease compared to inventive Example 1 | 9.3% increase compared to inventive Example 1. | Compared to Example 1, decrease in select |

The invention claimed is:

1. A composition, comprising a blended product of:
   (i) a first catalyst component, represented by a general formula (I): $(AE_aRE1_bRE2_cAT_dO_x)$, wherein,
      (a) 'AE' represents an alkaline earth metal; (b) 'RE1' represents a first rare earth element;
      (c) 'RE2' represents a second rare earth element; and (d) 'AT' represents a third rare earth element 'RE3' or a redox agent selected from antimony, tin, nickel, chromium, molybdenum, tungsten; wherein, 'a', 'b', 'c' and 'd' represents relative molar ratio; wherein 'a' is 1; 'b' ranges from 0.1 to 10; 'c' ranges from about 0.01 to about 10; 'd' ranges from 0 to about 10; 'x' balances the oxidation state; and wherein, the first rare earth element, the second rare earth element and the third rare earth element, are different; and
   (ii) a second catalyst component, represented by a general formula (II): $((AM)_2WO_4)e/SiO_2$; wherein,
   $(AM)_2WO_4$ represents an alkali metal tungstate, wherein, 'AM' represents an alkali metal; wherein, 'e' represents relative weight ratio and ranges from about 0.02 to about 0.8; and wherein, the composition has a catalyst activity for the reaction of oxygen and methane of at least 100 times greater than that of the catalyst activity of the second catalyst component.

2. The composition of claim 1, wherein the relative molar ratio 'b' ranges from 0.5 to 8.

3. The composition of claim 1, wherein the alkali metal tungstate is selected from the group consisting of lithium tungstate, sodium tungstate, potassium tungstate, rubidium tungstate, caesium tungstate and combinations thereof.

4. The composition of claim 1, wherein the first catalyst component is present in an amount ranging from about 5 wt. % to about 95 wt. % of the total weight of the composition.

5. The composition of claim 1, wherein the second catalyst component is present in an amount ranging from about 5 wt. % to about 95 wt. % of the total weight of the composition.

6. The composition of claim 1, wherein the alkaline earth metal is selected from the group consisting of magnesium, calcium, strontium, barium, and combinations thereof.

7. The composition of claim 1, wherein the first rare earth element, the second rare earth element, and the third rare earth element are each independently selected from the group consisting of lanthanum, scandium, cerium, praseodymium, neodymium, promethium, samarium, europium, gadolinium, yttrium, terbium, dysprosium, holmium, erbium, thulium, ytterbium, lutetium, and combinations thereof.

8. The composition of claim 1, wherein the composition has a 90% oxygen conversion temperature (T(90%)° C.) ranging from 0% to about 20%, greater than 90% oxygen conversion temperature (T(90%)° C.) of the first catalyst component.

9. The composition of claim 1, wherein the composition achieves a methane conversion ranging from about 10% to about 50%, when the composition is used in a process for producing $C_{2+}$ hydrocarbons from methane and oxygen.

10. The composition of claim 1, wherein the composition has an effective $C_{2+}$ hydrocarbon selectivity greater than 70% of product formed, when the composition is used in a process for producing $C_{2+}$ hydrocarbons from methane and oxygen.

11. The composition of claim 10, wherein the composition has an effective $C_{2+}$ hydrocarbon selectivity ranging from about 1% to about 10%, greater than effective $C_{2+}$ hydrocarbon selectivity of the first catalyst component.

12. The composition of claim 10, wherein the composition has a catalyst activity of at least four times that of a redox agent promoted second catalyst component.

13. A method for preparing the composition of claim 1, comprising: (a) blending the first catalyst component in an amount ranging from about 5 wt. % to about 95 wt. % of the composition with the second catalyst component in an amount ranging from about 95 wt. % to about 5 wt. % of the composition, and (b) forming the composition.

14. A composition comprising a $C_{2+}$ hydrocarbon mixture product, wherein the composition is formed using the composition of claim 1.

15. The composition of claim 14, wherein the $C_{2+}$ hydrocarbon mixture product comprises ethylene, ethane, ethyne, propene, propane, $C_4$-$C_5$ hydrocarbons, carbon dioxide, carbon monoxide and combinations thereof.

16. A process for producing a $C_{2+}$ hydrocarbon mixture product comprising: (a) introducing a feed mixture comprising methane and oxygen in a reactor containing the composition of claim 1; (b) subjecting the feed mixture to a methane coupling reaction under conditions suitable to produce the $C_{2+}$ hydrocarbon mixture product ; and (c) recovering the $C_{2+}$ hydrocarbon mixture product after removing unconverted methane and steam from the $C_{2+}$ hydrocarbon mixture product.

17. The process of claim 16, wherein methane to oxygen ratio ranges from about 2:1 to about 15:1.

18. The process of claim 16, wherein the $C_{2+}$ hydrocarbon mixture product is produced at a reactor temperature ranging from about 400° C. to about 900° C.

19. A composition, comprising a blended product of:
   (i) a first catalyst component represented by a general formula (I): $(AE_aRE1_bRE2_cAT_dO_x)$; wherein,
      (a) 'AE' represents an alkaline earth metal; (b) 'RE1' represents a first rare earth element;

(c) 'RE2' represents a second rare earth element; and (d) 'AT' represents a third rare earth element 'RE3' or a redox agent selected from antimony, tin, nickel, chromium, molybdenum, tungsten; wherein, 'a', 'b', 'c' and 'd' represents relative molar ratio; wherein 'a' is 1; 'b' ranges from 0.45 to about 10; 'c' ranges from about 0.01 to about 10; 'd' ranges from 0 to about 10; 'x' balances the oxidation state; wherein, the first rare earth element, the second rare earth element and the third rare earth element, are different and the first rare earth element, the second rare earth element, and the third rare element are each independently selected from the group consisting of lanthanum, scandium, cerium, praseodymium, neodymium, promethium, samarium, europium, gadolinium, yttrium, terbium, dysprosium, holmium, erbium, thulium, ytterbium, lutetium, and combinations thereof; and wherein, the first catalyst component is present in an amount ranging from about 5 wt. % to about 95 wt. % of the total weight of the composition; and (ii) a second catalyst component represented by a general formula (II): $((AM)_2WO_4)e/SiO_2$; wherein, $(AM)_2WO_4$ represents an alkali metal tungstate; wherein, 'AM' represents alkali metal and wherein, 'e' represents relative weight ratio and ranges from about 0.02 to about 0.8; and wherein, the second catalyst component has a catalyst activity for oxidative coupling of methane of less than 1% of catalyst activity for oxidative coupling of methane of the composition; wherein the second catalyst component is present in an amount ranging from about 5 wt. % to about 95 wt. % of the total weight of the composition; wherein, the composition has a 90% oxygen conversion temperature (T(90%)° C.) ranging from 0% to about 20% greater than 90% oxygen conversion temperature (T(90%)° C.) of the first catalyst component; and wherein, the composition has a catalyst activity for the reaction of oxygen and methane of at least 100 times greater than that of the catalyst activity of the second catalyst component.

* * * * *